US011052029B2

(12) United States Patent
Miller

(10) Patent No.: US 11,052,029 B2
(45) Date of Patent: Jul. 6, 2021

(54) CATION COMPATIBLE METAL OXIDES AND ORAL CARE COMPOSITIONS CONTAINING THE METAL OXIDES

(71) Applicant: W. R. Grace & Co.-Conn., Columbia, MD (US)

(72) Inventor: James George Miller, Ellicott City, MD (US)

(73) Assignee: W. R. Grace & Co.-Conn., Columbia, MD (US)

( * ) Notice: Subject to any disclaimer, the term of this patent is extended or adjusted under 35 U.S.C. 154(b) by 26 days.

(21) Appl. No.: 14/971,343

(22) Filed: Dec. 16, 2015

(65) Prior Publication Data
US 2016/0095805 A1 Apr. 7, 2016

Related U.S. Application Data

(62) Division of application No. 13/378,390, filed on Dec. 15, 2011, now abandoned.

(60) Provisional application No. 61/187,433, filed on Jun. 16, 2009.

(51) Int. Cl.
| | |
|---|---|
| *A61K 8/49* | (2006.01) |
| *A61K 8/02* | (2006.01) |
| *A61K 8/67* | (2006.01) |
| *A61K 8/25* | (2006.01) |
| *A61Q 11/00* | (2006.01) |

(52) U.S. Cl.
CPC .......... *A61K 8/4926* (2013.01); *A61K 8/0241* (2013.01); *A61K 8/25* (2013.01); *A61K 8/673* (2013.01); *A61Q 11/00* (2013.01); *A61K 2800/56* (2013.01)

(58) Field of Classification Search
None
See application file for complete search history.

(56) References Cited

U.S. PATENT DOCUMENTS

| | | | |
|---|---|---|---|
| 4,029,513 A | 6/1977 | Vessey et al. | 106/288 |
| 4,110,083 A * | 8/1978 | Benedict | A61K 8/19 424/49 |
| 4,617,294 A * | 10/1986 | Krivak | A01C 5/068 426/72 |
| 5,174,989 A * | 12/1992 | Tanaka | A61K 8/21 131/270 |
| 5,178,869 A | 1/1993 | Ebine et al. | 424/401 |
| 5,180,585 A | 1/1993 | Jacobson et al. | 424/405 |
| 5,747,003 A | 5/1998 | Mahnot et al. | 424/49 |
| 6,355,229 B1 * | 3/2002 | Adamy | A61K 8/416 424/435 |
| 6,716,513 B1 | 4/2004 | Hasuo et al. | 428/141 |
| 6,746,681 B1 | 6/2004 | Carroll et al. | 424/401 |
| 6,960,251 B2 | 11/2005 | Uhrlandt et al. | 106/482 |
| 7,255,852 B2 * | 8/2007 | Gallis | A61K 8/25 423/335 |
| 7,569,274 B2 * | 8/2009 | Besse | A61K 9/143 427/212 |
| 7,731,790 B2 | 6/2010 | Viot | 106/491 |
| 2001/0051176 A1 | 12/2001 | Viot | 424/439 |
| 2005/0031551 A1 * | 2/2005 | Prencipe | A61K 8/25 424/49 |
| 2006/0246149 A1 | 11/2006 | Buchholz et al. | 424/603 |
| 2007/0140984 A1 * | 6/2007 | Kusano | A61K 8/602 424/49 |
| 2008/0293955 A1 | 11/2008 | Riihle et al. | 549/408 |

FOREIGN PATENT DOCUMENTS

| | | | |
|---|---|---|---|
| EP | 0396460 | 7/1990 | ........... C01B 33/193 |
| WO | 1993/23007 | 11/1993 | ............... A61K 8/21 |
| WO | 2003/037285 | 5/2003 | ............... A61K 8/21 |
| WO | 2004/073380 | 9/2004 | ............... A61K 7/16 |
| WO | 2004/073539 | 9/2004 | |
| WO | 2005/000253 | 1/2005 | |
| WO | 2007/011552 | 1/2007 | ............. A61Q 11/00 |
| WO | 2007/135196 | 11/2007 | ........... A61K 8/4946 |
| WO | 2008/082758 | 7/2008 | ............... A61K 8/19 |
| WO | 2008/082795 | 7/2008 | ............... A61K 8/00 |

OTHER PUBLICATIONS

Slavinskaya et al., Physical Chemistry of Surface Phenomena, 80: 1305-1308 (2006).*
Goloub et al., Langmuir et al., 13: 673-681 (Year: 1997).*
Nguyen et al., Physical Review Letters, 85: 1568-1571 (Year: 2000).*
Besteman et al., Physical Review E, 72: 601501-1 (Year: 2005).*
Goloub et al., Langmuir, 12: 3188-3194 (Year: 1996).*
Stanvinskaya et al. ("Adsorption Properties of Highly Dispersed Silica with a Partially Hydrophobic Surface," 2006, PLEIADES; Russian Journal of Physical Chemistry, vol. 80, No. 8, pp. 1482-1485.*
Rajh, T. et al. "Improving Optical and Charge Separation Properties of Nanocrystalline TiO2 by Surface Modification with Vitamin C". Journal of Physical Chemistry J. Phys. Chem. B. 1999, 103, 3515-3519.
Rodrigues, Flavio A. et al. "The Alkali-Silica Reaction. The Surface Charge Density of Silica and Its Effect on Expansive Pressure". Cement and Concrete Research 29 (1999) 527-530.
Wu, Zhijian et al."Effects of Surface Coating on the Controlled Release of Vitamin B1 from Mesoporous Silica Tablets", ScienceDirect, Journal of Controlled Release 119 (2007) 215-221.
European Search Report for EP10790123.3; dated Apr. 21, 2015.
PCT Search Report for PCT/US2010/038837; dated Dec. 23, 2010.
Kosmulski, Merck "pH-Dependent Surface Charging and Points of Zero Charge. IV. Update and New Approach". Journal of Colloid and Interface Science 337 (2009) 439-448.

* cited by examiner

*Primary Examiner* — David J Blanchard
*Assistant Examiner* — Ivan A Greene

(57) ABSTRACT

A cationic compatible metal oxide and oral care compositions containing the metal oxide are disclosed. Preferably, the oral care compositions contain a cationic compatible metal oxide and a cationic ingredient, such as for example, a cationic antibacterial agent such as cetyl pyridinium chloride ("CPC"). The cationic compatible metal oxide, e.g. silica, comprise metal oxide particles having a substantially negative surface charge and a vitamin deposited onto or reacted with the surface of the metal oxide particles in an amount sufficient to provide a substantially positive surface charge on the metal oxide particle. Processes for making and using the vitamin modified metal oxide in oral care compositions are also disclosed.

14 Claims, No Drawings

CATION COMPATIBLE METAL OXIDES AND ORAL CARE COMPOSITIONS CONTAINING THE METAL OXIDES

This patent application is a divisional patent application of U.S. Utility patent application Ser. No. 13/378,390 entitled "CATION COMPATIBLE METAL OXIDES AND ORAL CARE COMPOSITIONS CONTAINING THE METAL OXIDES" and filed on Dec. 15, 2011, which is the U.S. national stage application of and claims the benefit of priority to International Patent Application Serial No. PCT/US2010/038837 entitled "CATION COMPATIBLE METAL OXIDES AND ORAL CARE COMPOSITIONS CONTAINING THE METAL OXIDES" and filed on Jun. 16, 2010, which claims the benefit of priority to U.S. Provisional Patent Application Ser. No. 61/187,433 entitled "CATION COMPATIBLE METAL OXIDES AND ORAL CARE COMPOSITIONS CONTAINING THE METAL OXIDES" and filed on Jun. 16, 2009, the subject matter of which are hereby incorporated by reference in their entirety.

FIELD OF THE INVENTION

The present invention relates to a cationic compatible modified metal oxide and to a process of making and using the modified metal oxide in oral care compositions. In particularly, the present invention relates to oral care compositions containing a cationic compatible modified metal oxide and a cationic antibacterial agent, and to processes for making and using said compositions.

BACKGROUND OF THE INVENTION

Oral care compositions, e.g. dentifrices, often contain an abrasive substance for controlled mechanical cleaning and polishing of teeth. Metal oxide particles, e.g. silica, are often used as an abrasive in oral care compositions. For example, silica's abrasive action is used for pellicle removal from teeth in dentifrice. Most conventional silicas used in dentifrices have negatively-charged surfaces.

There is an increased desire to incorporate antimicrobial agents in oral care compositions for the control of malodor and/or other therapeutic action. Cetyl pyridinium chloride ("CPC") is often used as an antimicrobial agent for this purpose. CPC is a cationic ("positively") charged compound. CPC's antimicrobial action is generally understood to result from its ability to bind to anionically ("negatively") charged protein moieties on bacterial cells present in the mouth. This CPC attachment mechanism results in a disruption of normal cellular function of bacteria and contributes to the prevention of plaque formation and other bacterial actions.

A problem encountered in CPC usage in oral care compositions has been that CPC tends to indiscriminately bind to negatively-charged surfaces. For example, metal oxide particles, e.g. silica particles, which are often used in oral care compositions as an abrasive, have a negatively charged surface and may bind to CPC. Once bound to the metal oxide particles, or other negatively charged co-ingredients, CPC is generally unavailable to perform any meaningful antimicrobial action.

Several patent publications have described compositions and processes for the preparation of CPC compatible, oral care compositions.

For example, U.S. Pat. No. 6,355,229 describes a CPC compatible dentifrice formulation containing guar hydroxypyropyl-trimonium chloride. The guar complex has a higher affinity toward binding to negatively-charged species than CPC. It preferentially binds to anionic components leaving CPC free to bind to plaque.

WO2004/073539A discloses a precipitated silica comprising porous silica particles having a cumulative surface area for all pores having diameters greater than 500 Å of less than 8 m$^2$/g and a percentage CPC compatibility of greater than about 55%. The precipitated silica product is well adapted for use in dentifrices containing CPC since CPC does not attach to the low surface area silica product.

A need still exists in the industry for metal oxides that can be used together with cationic anti-microbial agents such as CPC in oral compositions without impairment of the respective functions of either ingredient. The present invention meets these needs and others as will become readily apparent from the following disclosure.

SUMMARY OF THE INVENTION

It has now been discovered that the problem of cationic molecule-metal oxide incompatibility can be overcome in oral care formulations by the use of a cationic-compatible, modified metal oxide component. Unexpectedly it has been found that the treatment of negatively charged metal oxide particles such as silica with an essential vitamin molecule sufficiently alters the surface charge of metal oxide particles to provide a substantially positive charge on the surface on the treated metal oxide particle. The positively charged vitamin treated metal oxide surface minimizes adsorption of or reaction with CPC and other positively-charged ingredients typically used in oral care compositions, thereby promoting the availability of both the antibacterial agents and the metal oxide particles to perform their respective intended functions in the oral care compositions.

The cationic compatible modified metal oxide is formed by immobilizing, e.g. by reacting and/or adsorbing, a vitamin molecule directly onto the surface of a negative surface charged metal oxide particle. The vitamin treated metal oxide of the invention is particularly useful as a cationic compatible abrasive or thickening agent in oral care compositions, e.g. dentifrices, comprising CPC and other cationic antibacterial agents. Oral care compositions comprising the vitamin treated metal oxide of the invention and one or more cationic active antibacterial agent provide the benefits of increased compatibility with minimal safety risks associated with the leaching of components of the oral care compositions during human use or consumption.

Accordingly, it is an advantage of the present invention to provide a negative surface charged metal oxide material which is compatible with CPC and other cationic antibacterial agents.

It is also an advantage of the present invention to provide novel oral care compositions comprising cationic-compatible metal oxides.

It is also an advantage of the present invention to provide novel oral care compositions comprising cationic compatible silica.

Another advantage of the present invention is to provide oral care compositions comprising a cationic compatible metal oxide and a cationic antibacterial agent, e.g. CPC, wherein the reaction of the metal oxide and the antibacterial agent is minimized.

Yet another advantage of the present invention is to provide oral care compositions comprising a cationic compatible silica and a cationic antibacterial agent, e.g. CPC, wherein the reaction of silica and the antibacterial agent is minimized.

It is also an advantage of the present invention to provide a method of preparing an oral care composition comprising vitamin-modified negative surface charged metal oxides, e.g. silica, and a cationic antibacterial agent, e.g. CPC, wherein the reaction of the metal oxide and the antibacterial agent is minimized.

Yet another advantage of the present invention is to provide processes of using compositions and processes in accordance with the present invention.

These and other aspects of the present invention are described in further detail below.

DETAILED DESCRIPTION OF THE INVENTION

The present invention is directed to a cationic compatible metal oxide which is particularly useful in oral care compositions containing positively charged molecules, in particularly, antibacterial agents such as, for example, CPC. The cationic compatible metal oxide is formed by attaching a suitable vitamin molecule onto the surface of the metal oxide particles to provide a substantially positive charge on the surface of the metal oxide particles. For purposes of this invention the term "substantially positive charge" is used herein to indicate a positive charge sufficient to repel and/or minimize the reaction with cationic molecules.

Metal oxide particles suitable for use in the present invention include particles of any metal oxide having a negatively charge surface under the conditions of use. Typically, the metal oxide will have an isoelectric point of less than 8, preferably, less than 5 and most preferably less than 3. Suitable metal oxides include, but are not limited to, a metal oxide selected from the group consisting of silica, titanic, zirconia, silica alumina and mixtures thereof. The term "silica alumina" is used herein to include an amorphous silica alumina or crystalline silica alumina such as zeolites.

In accordance with the present invention, the surface of negatively charged metal oxide particles is made substantially positive by treating the metal oxide to immobilize a desired vitamin molecule onto the surface of the metal oxide particles. For purposes of the invention, the term "immobilize" is used to indicate that the vitamin is adsorbed onto or chemically reacted with the surface of the metal oxide particles. The vitamin treatment of the metal oxide alters the negative charge on the metal oxide surface to a substantially positive charge. The presence of the positive charge on the surface of the treated metal oxide promotes cationic compatibility by repelling and/or minimizing reaction with cationic molecules, i.e. molecules having a positive charge.

Although the exact mechanism of attachment of the vitamin onto the metal oxide surface is not known, it is hypothesized that the vitamin molecule may be chemically attached to the metal oxide surface by reaction of an alcohol group on the vitamin molecule with the surface hydroxyl group on the metal oxide surface to form an ester bond. Another mechanism of attachment may be the physical adsorption of the vitamin molecule onto the metal oxide surface due to the polar nature of the vitamin molecule.

In a preferred embodiment of the invention, the metal oxide particles comprise silica particles. For purposes of the present invention, the term "silica particles" is used herein to indicate finely divided silica, silica primary particles, silica aggregates (i.e., unitary clusters of a plurality of silica primary particles), and silica agglomerates (i.e., unitary clusters of a plurality of silica aggregates), singly or in combinations thereof.

Silica particles useful in the present invention may be any silica particle having sufficient mechanical integrity to promote pellicle removal in an oral care composition. Typically, silica particles useful in the present invention have a BET surface area in the range of about 1 $m^2/g$ to about 200 $m^2/g$, preferably about 10 $m^2/g$ to about 50 $m^2/g$, and median agglomerates sizes in the range of about 1μ to about 20μ, preferably from about 3μ to about 15μ.

Silicas useful in the present invention include, but are not limited to, natural amorphous silica, for instance diatomaceous earth; or synthetic amorphous silica, for instance precipitated silica or silica gel, such as a silica xerogel, or mixtures thereof. The preferred grades of synthetic amorphous silicas are those for which the manufacturing process is carefully controlled so that the level of anion impurities, particularly sulphate and silicate from sodium sulphate and sodium silicate, respectively, is kept to a minimum. Alternatively, or in addition, the level of anion impurities may be reduced to the required level by careful washing of the silica with, for instance, deionised or distilled water. In a preferred embodiment of the invention, the silica is precipitated silica.

Silicas useful in the present invention may be prepared as precipitates or gels from silicate and acid by conventional means, the crude silica product being collected and then washed with water, preferably deionised water, until the conductivity of the washings is less than 200 microsiemens $cm^{-1}$, preferably less than 100 microsiemens $cm^{-1}$, and then dried and, if necessary, ground, to give the desired sizes of particles. Alternatively, an initial washing of the crude product with water, until the washings have a conductivity of less than 2000 microsiemens $cm^{-1}$, may be followed by washing with an acid or an aqueous acid, for instance a mineral acid such as nitric acid, or an organic acid such as acetic acid or citric acid, until the silica has a pH of less than 8, preferably between 6 and 7.6.

Vitamin molecules useful in the present invention include any vitamin molecule which may be immobilized on the surface of a negatively charged metal oxide particle to form a substantially positive charge on the surface of the metal oxide particle. In a preferred embodiment of the invention, the vitamin molecule is immobilized on the metal oxide particle, e.g. a silica particle, by adsorbing the vitamin directly onto the surface of the particle or by reacting the vitamin directly with the surface of the particle. Suitable vitamins include, for example, vitamin B, vitamin M (folic acid), vitamin U and their salts and derivatives. The term "vitamin B" is used in the present invention to indicate vitamins of the vitamin B family such as vitamin B1 (thiamine), vitamin B2 (riboflavin), vitamin B3 (niacin), vitamin B4 (adenine), vitamin B6 (pyridoxine) and salts thereof.

In a preferred embodiment of the present invention, the vitamin is a vitamin B. Most preferably, the vitamin is a vitamin B selected from the group consisting of vitamin B1, vitamin B2, vitamin B6, salts thereof, and mixtures thereof.

In accordance with the present invention, the vitamin is immobilized on the surface of the metal oxide particles by contacting the negative surface charged metal oxide with the desired vitamin using conventional techniques. In one embodiment of the invention, the metal oxide particles are slurried in an aqueous solution, preferably water, containing a concentration of the desired vitamin sufficient to provide a substantially positive charge on the surface of the treated metal oxide. Preferably the aqueous solution contains a concentration of from about 0.01 wt % to fully saturated of the vitamin depending on the inherent solubility of the vitamin in the aqueous solution. For example, when the vitamin is vitamin B1, the concentration ranges from about 0.01 wt % to about 50 wt %; when the vitamin is vitamin B6, the concentration ranges from about 0.01 wt % to about 23 wt %. The metal oxide particles are contacted with the aqueous vitamin solution for a time and at a temperature sufficient to react and/or adsorb an amount of the vitamin sufficient to provide a positive or substantially positive charge on the surface of the metal oxide particles. Preferably, the metal oxide particles are contacted with the aqueous vitamin solution for about 1 minute to about 72 hours and at a temperature ranging from about ambient temperature to about 98° C.

The slurry of treated metal oxide is then typically filtered and washed to remove residues. After washing the filter cake is dried for a time and at a temperature sufficient to remove water and form a powder of treated metal oxide particles, typically at a temperature ranging from about 60° C. to about 120° C. for about 1 minute to about 4 hours. Optionally, the dried metal oxide particles are comminuted by conventional means, e.g. air milling or mechanical milling, to a desired particle size, e.g., less than 20 micron, preferably, less than 15 microns.

Alternatively, the vitamin modified metal oxide particles may be formed by first dispensing the metal oxide particles in an aqueous solution, preferably water, to form a slurry and thereafter, adding a sufficient amount of the vitamin to the slurry to fully disperse the vitamin and provide the desired concentration of vitamin in the slurry. Thereafter, the vitamin containing slurry is mixed for a time and at a temperature sufficient to react and/or adsorb an amount of the vitamin sufficient to provide a positive or substantially positive charge on the surface of the metal oxide particles, e.g., from about ambient temperature to about 98° C. for about 1 minute to about 72 hours. The vitamin treated metal oxide particles obtained are then filtered, washed, dried and optionally, comminuted to a desired particle size.

Another method for immobilizing the vitamin molecules on the surface of the metal oxide particles include impregnating the metal oxide particles with a vitamin containing solution, preferably, an aqueous solution, to partially or completely fill the pores of the metal oxide particles. Preferably the vitamin containing solution has a concentration of from about 0.01 wt % to fully saturated of the vitamin depending on the inherent solubility of the vitamin in the solution medium. The impregnated metal oxide material is subsequently dried to remove excess water. Optionally, the dried metal oxide material is suspended in water, filtered and washed to remove excess vitamin solution. Thereafter, the metal oxide material is dried and optionally comminuted as described here in above to obtain a desired particle size.

It is also within the scope of the present invention to affect treatment of the metal oxide particles with the vitamin molecules during the manufacture process to produce the metal oxide. For example, the treatment of silica particles with the vitamin molecule may be accomplished during the conventional preparation of silicas typically used in an oral care composition. During the preparation of a precipitated silica, for example, an aqueous slurry containing the silica is formed. The vitamin, or an aqueous solution thereof, is incorporated into the aqueous silica slurry and mixed for a time and at a temperature sufficient to provide a substantially positive charge on the surface of the silica particles, e.g. at a temperature ranging from about ambient temperature to about 98° C. for about 1 minute to about 72 hours. The slurry of treated silica is thereafter, washed, filtered, dried and optionally, comminuted as described herein above.

In general, the vitamin treated metal oxide contains a concentration of the desired vitamin sufficient to provide a substantially positive surface charge on the metal oxide. Typically, where the metal oxide is silica, the concentration of vitamin on the silica will range from about 0.01 to about 10.0 wt %, preferably from about 0.015 to about 5.0 wt %, most preferably from about 0.5 to 1 wt %, of the total silica composition.

Oral care compositions contemplated for incorporation of the cationic compatible metal oxide of the present invention include, for example, dentifrices, chewing gums, and mouthwashes, and the like. The term "dentifrice" means oral care products in general such as, without intending to be limited, toothpastes, tooth powders, and denture creams.

The vitamin treated metal oxide particles, in particular vitamin treated silica particles, of the invention may also have broader cleaning utility and application, including, for instance, as a metal, ceramic or porcelain cleaning or scrubbing agent.

Preferably, oral care compositions in accordance with the invention comprise particulate silica and a cationic antibacterial agent wherein the silica particles comprise on the surface thereof a vitamin molecule in an amount sufficient to provide a substantially positive charge on the surface of the silica particles. The presence of the vitamin molecules have been shown to markedly increase the compatibility of the silica with cationic antibacterial agents, in particularly CPC, as demonstrated by compatibility test defined in the Examples hereinbelow.

For purposes of the present invention the term "% CPC compatibility" is used to indicate the molar percentage of CPC available in solution after contacting 3 g of vitamin treated silica with 27 g of 0.3 wt % CPC solution for 7 days at 140° F. The molar concentration is determined by measuring the UV absorbance peak at 259 nm using a UV-Visible spectrometer. Generally, the vitamin-treated silica has a % CPC compatibility of at least 10%, preferably at least 50%; most preferably at least 60%. It is believed that a compatibility with CPC is indicative of the compatibility with cationic antibacterial agents in general. Preferably, the % CPC compatibility of the vitamin-treated metal oxide ranges from about 10% to about 100%; most preferably, from about 20% to about 80%.

Oral care compositions incorporating the vitamin-treated metal oxide product described herein above preferably comprise CPC in an antimicrobial effective amount. This amount can vary, depending on other ingredients of the formulation and limitations placed upon its use by regulating authorities (e.g. FDA), but generally the amount will range from about 0.01 to about 1 wt %, preferably from about 0.1 to about 0.75 wt %, most preferably from about 0.25 to 0.50 wt %.

CPC is used herein as representative of a cationic antibacterial agent. Any suitable cationic antimicrobial agent is contemplated by the invention. Other suitable cationic antibacterial agents include, but are not limited to, chlorhexidine and chlorhexidine gluconate; benzalkonium chloride (BZK); benzethonium chloride (BZT); domiphen bromide; and metal salts such as zinc chloride, citrate or gluconate and stannous chloride and fluoride. If present, the additional cationic antibacterial agents generally comprise up to about 2 wt % of the oral care compositions. Preferably, the antibacterial agents comprises from about 0.01 to 1 wt %, most preferably, from about 0.1 to about 0.75 wt % of the oral care composition.

Other additives commonly used or otherwise beneficial in oral care compositions may optionally be included in the oral care formulation. A pharmaceutically acceptable carrier for the components of oral compositions containing the silica product of the present invention is optional and can be any vehicle suitable for use in the oral cavity of a human or other warm blood animal. Such carriers include, but are not limited to, the conventional components of toothpastes, tooth powders, prophylaxis pastes, lozenges, gums, and the like and are more fully described thereafter.

Flavoring agents optionally can be added to oral care compositions. Suitable flavoring agents include oil of wintergreen, oil of peppermint, oil of spearmint, oil of sassafras, and oil of clove, cinnamon, anethole, menthol, and other such flavor compounds to add fruit notes, spice notes, etc. These flavoring agents consist chemically of mixtures of aldehydes, ketones, esters, phenols, acids, and aliphatic, aromatic and other alcohols.

Sweetening agents, which can be used, include aspartame, acesulfame, saccharin, dextrose, levulose and sodium cyclamate. Flavoring and sweetening agents are generally used at levels of from about 0.005% to about 2% by weight of the oral care compositions.

A water-soluble fluoride supplying compound may optionally be added and present in the oral care compositions in an amount sufficient to provide a fluoride Ion concentration in the composition at 25° C., and/or when it is used for its intended use, of from about 0.0025% to about 5.0% by weight, preferably from about 0.005% to about 2.0% by weight, to provide additional anticaries effectiveness. A wide variety of fluoride ion-yielding materials may be employed as sources of soluble fluoride in present compositions. Examples of suitable fluoride ion-yielding materials are found in U.S. Pat. Nos. 3,535,421 and 3,678,154, both being incorporated herein by reference. Representative fluoride ion sources include: stannous fluoride, sodium fluoride, potassium fluoride, sodium monofluorophosphate and many particularly preferred, as well as mixtures thereof.

Water is also present in the oral care compositions in amounts which are dependent on the intended use of the compositions. For example, water employed in the preparation of suitable toothpastes should preferably be deionized and free of organic impurities. Water generally comprises from about 2% to 50%, preferably from about 5% to 20%, by weight, of the toothpaste compositions. These amounts of water include the free water which is added plus that which is introduced with other additives and materials, such as humectant.

It may be necessary to add some thickening or binder material to the oral care compositions depending upon the intended use. For example, in preparing toothpastes, thickening and binder material are often required to provide a desirable consistency and thixotropy. Preferred thickening agents are carboxyvinyl polymers, carrageenan, hydroxyethyl cellulose and water-soluble salts of cellulose ethers such as sodium carboxymethyl cellulose and sodium carboxymethyl hydroxyethyl cellulose. Natural gums such as gum karaya, xanthan gum, gum Arabic, and gum tragacanth can also be used. Thickening agents in an amount from about 0.5% to about 5.0% by weight of the total composition generally can be used.

Silica thickeners can also be used in the oral care compositions provided however that the silica is treated with a vitamin as described in the present invention. Typical silica thickeners include, but are not limited to, precipitated silica, silica gels and fumed silica. Silica thickeners can be added generally at a level of about 5% to about 15% by weight.

It is also often desirable to include some humectant material in an oral care composition, e.g. toothpaste, to keep It from hardening. Suitable humectants include glycerin (glycerol), sorbitol, polyalkylene glycols such as polyethylene glycol and polypropylene glycol, hydrogenated starch hydrolyzates, xylitol, lactitol, hydrogenated corn syrup, and other edible polyhydric alcohols, used singly or as mixtures thereof. Suitable humectants can be added generally at a level of from about 15% to about 70% by weight.

Chelating agents optionally can be added to the oral care compositions of the invention, such as alkali metal salts of tartaric acid and citric acid, or alkali metal salts of pyrophosphates or polyphosphates.

Other optional ingredients and adjuvants of oral care compositions, e.g., dentifrices such as those described in U.S. Pat. No. 5,676,932 and Pader, M., Oral Hygiene Products and Practice, Marcel Dekker, Inc., New York, 1988, for instance, also can be added as needed or desired. These other optional adjuvants, additives, and materials that can be added to the oral care compositions of the present invention include, for example, foaming agents (e.g., sodium lauryl sulfate), detergents or surfactants, coloring or whitening agents (e.g., titanium dioxide, FD&C dyes), preservatives (e.g., sodium benzoate, methyl paraben), chelating agents, antimicrobial agents, and other materials that can be used in oral care compositions. The optional additives, if present, generally are present in small amounts, such as no greater than about 6% by weight each.

In all cases, the ingredients used in oral care formulations, such as thickening gums, foaming agents, and the like, are selected to be compatible with the therapeutic agents and flavors.

A safe and effective amount of the compositions of the present invention may be applied for use in a warm-blooded animal, preferably a human, in several conventional ways. In general, compositions of the present invention are topically applied to the muscosal tissue of the oral cavity, to the gingival tissue of the oral cavity, and/or to the tooth surface, for reducing the levels of undesirable oral microorganisms residing thereon. For example, the gingival or mucosal tissue may be bathed in the liquid and/or latter generated by brushing of the teeth with a dentifrice (e.g. toothpaste, tooth gel or tooth powder) comprising compositions of the present invention. Other methods of applying the compositions of the invention to the gingival mucosal tissue and tooth surface are apparent to those skilled in the art depending on the desired use.

To further illustrate the present invention and the advantages thereof, the following specific examples are provided. The examples are given as specific illustrations of the claimed invention. It should be understood, however, that the invention is not limited to the specific details set forth in the examples below.

All parts and percentages in the examples as well as the remainder of the specification are by weight unless otherwise specified.

Further, any range of numbers recited in the specification or claims, such as that representing a particular set of properties, units of measure, conditions, physical states or percentages, is intended to literally incorporate expressly herein by reference or otherwise, any number falling within such range, including any subset of numbers within any range so recited.

The following examples are presented to illustrate the present invention, but the invention is not to be considered as limited thereby.

EXAMPLES

For the following examples, CPC compatibility of the untreated and treated silica material was obtained using the following procedure: In a plastic centrifuge tub place 3.0 g of silica along with 27.0 g of 0.3 wt % CPC solution. The tub was sealed with a cap and the contents of the tube mixed and placed in an oven at 130° F. to 140° F. After a desired period of time (about 3 hrs to about 8 days) the mixture was removed from the oven, cooled, and centrifuged at 10,000 rpm for 10 minutes. A sample (1.000 g) of the clear liquid formed above the solid silica layer in the centrifuge tube was carefully extracted and diluted 20:1 with DI (1.000 g clear liquid in 19.000 g DI water). The solution was then tested for its absorbance at 259 nm using a Shimadzu UV-1601 UV-visible spectrophotometer in 1 cm path length matched quartz cuvettes. CPC has a characteristic UV absorbance peak at 259 nm. This UV absorbance peak was used to determine the concentration of CPC remaining free in solution. The typical absorbance value for a reference 20:1 diluted 0.3 wt % CPC obtained at 259 (no silica present) is 1.87. The percent CPC freely remaining in solution after heating in the presence of silica, defined as the % CPG compatibility, was calculated as shown below:

% CPC compatibility=100×(sample solution absorbance at 259 nm)/1.78

Example 1

3.0 g of a precipitated silica and 27.0 g of 0.3 wt % CPC solution was placed in a plastic centrifuge tub. The properties of the precipitated silica were as follows: 11 micron APS, 31 m$^2$/g surface area, 0.1 cc/g N$_2$ pore volume. The tub was sealed with a cap and contents mixed and then placed in an oven at 140° F. After 6 days the mixture was taken out of the oven, cooled, and centrifuged at 10,000 rpm for 10 minutes. A 1.000 g sample of the clear liquid formed above the solid silica layer in the centrifuge tube was carefully extracted and diluted 20:1 by combining with 19.000 g of DI water. The resultant solution was transferred to a 1 cm quarts cuvette and the results are recorded in Table 1 below.

TABLE 1

| Time (at 140° F.) | UV Absorbance (259 nm) | CPC Compatibility (Ads 259 nm/1.78) × 100 |
| --- | --- | --- |
| 6 days | 0.0 | 0% |

The absorbance of the solution was measured at 259 nm. These results indicate that all the positively charged CPC molecules have been adsorbed by the untreated silica and are not freely available in solution.

Example 2

Thiamine HCL (18 g) was dissolved in 18.6 g of DI water in a 50 nil Erlenmeyer flask covered with a watch glass. Precipitated silica (4.0 g), having the following properties: 11 micron APS, 31 m$^2$/g surface area, 0.1 cc/g N2 pore volume, was added and the mixture was heated while stirring at −98 C. After 1 hr the mixture was filtered hot and washed 3 times with 50 ml portions of H$_2$O. The isolated solid was dried in a porcelain dish at 120° C. overnight. Percent CPC compatibility testing of the resultant solid is recorded in Table 2 below.

TABLE 2

| Time (at 130° F.) | UV Absorbance (259 nm) | CPC Compatibility (Ads 259 nm/1.78) × 100 |
| --- | --- | --- |
| 2 hrs | 1.224 | 69% |
| 3 days | 1.122 | 63% |
| 7 days | 1.115 | 63% |

As shown in Table 2, 69% of CPC was available in solution after 2 hrs. Impressively, however, after 3 and 7 days, respectively, 63% of the CPC was soluble and freely available in solution indicating that the CPC had not been substantially absorbed on surface of the thiamine treated silica.

Example 3

Thiamine HCL (20 g) was dissolved in 20 g of DI water in a 125 ml Erlenmeyer flask covered with a watch glass. 10.0 g of precipitated silica (10.0 g), having the following properties: 11 micron APS, 31 m2/g surface area, 0.1 cc/g N2 pore volume, was added and the mixture was heated while stirring at ~98 C. After heating for 7 hrs the mixture was filtered hot and washed 4 times with 100 ml portions of H$_2$O. The Isolated solid was dried in a porcelain dish at 120° C. overnight. The results of the percent CPC compatibility testing of the resultant solid are recorded in Table 3 below:

TABLE 3

| Time (at 140° F.) | UV Absorbance (259 nm) | CPC Compatibility (Ads 259 nm/1.78) × 100 |
| --- | --- | --- |
| 3 hrs | 1.122 | 63% |
| 8 days | 0.917 | 52% |

As clearly shown in Table 3, 52% of CPC was freely soluble and available in solution after 5 days.

Example 4

Thiamine HCL solution (1.94 g thiamine HCL in 18.4 g of DI water) was added drop wise to 20 g of precipitated silica (having the following properties: 11 micron APS, 31 m2/g surface area, 0.1 cc/g N2 pore volume) in a 50 ml beaker. The mixture was stirred with a spatula until a uniform paste consistency was formed. The material was transferred to a porcelain dish and dried at 120° C. for 4 hrs. The dried material was suspended in 100 ml of DI water and filtered using a Buchner funnel. The wet cake was then washed with 3 portions of 100 ml of DI H$_2$O and allowed at air dry on the filter. Percent CPC compatibility testing of the resultant solid is recorded in Table 4 below.

TABLE 4

| Time (at 130° F.) | UV Absorbance (259 nm) | CPC Compatibility (Ads 259 nm/1.78) × 100 |
| --- | --- | --- |
| 1 day | 1.095 | 62% |
| 7 days | 1.142 | 64% |

As shown in Table 4, the percent CPC compatibility was 62% after 1 day at 130° F. and 64% after 7 days at 130° F. These results evidenced that CPC remained unabsorbed by the thiamine treated silica and was soluble and available in solution.

Example 5

Pyridoxine (2.02 g) was dissolved in 18.11 g of DI water in a 125 ml Erlenmeyer flask covered with a watch glass. 4.03 g of precipitated silica (having the following properties: 11 micron APS, 31 m2/g surface area, 0.1 cc/g N2 pore volume) was added and the mixture was heated while stirring at ~98 C. After heating for 6 hrs the mixture was filtered hot and washed 4 times with 100 ml portions of $H_2O$. The isolated solid was dried in a porcelain dish at 120° C. overnight. Percent CPC compatibility testing of the resultant solid is recorded in Table 5 below.

TABLE 5

| Time (at 130° F.) | UV Absorbance (259 nm) | CPC Compatibility (Ads 259 nm/1.78) × 100 |
|---|---|---|
| 7 days | 1.12 | 63% |

As shown in Table 5, the percent CPC compatibility was 63% after 7 days at 140° F. These results indicate that after 7 days, 63% of the CPC remained unabsorbed by the pyridoxine treated silica and were soluble and freely available in the solution.

What is claimed is:

1. An oral care composition comprising:
   (1) an antibacterial effective amount of at least one cationic antibacterial agent, wherein the at least one cationic antibacterial agent is cetyl pyridinium chloride (CPC); and
   (2) a cationic compatible metal oxide comprising (i) a silica particle having a negative surface charge and (ii) a vitamin B1 molecule immobilized on the surface of the silica particle so as to form a vitamin B1 treated silica particle, the vitamin B1 molecule (a) comprising (i) a vitamin with an overall positive charge or (ii) a salt of a vitamin, the salt having an overall positive charge, (b) being present in an amount sufficient to provide a substantially positive charge on the surface of the vitamin B1 treated silica particle, and (c) being present in an amount sufficient to repel or minimize any reaction of the silica particle with said cetyl pyridinium chloride (CPC).

2. The oral care composition of claim 1, wherein the amount of vitamin B1 molecule immobilized on the surface of the silica particle ranges from about 0.01 wt % to about 10.0 wt % of the silica particle.

3. The oral care composition of claim 2, wherein the vitamin B1 molecule is immobilized directly onto the surface of the silica particle.

4. The oral care composition of claim 3, wherein the vitamin B1 molecule is impregnated onto the surface of the silica particle.

5. The oral care composition of claim 3, wherein the vitamin B1 molecule is adsorbed directly onto the surface of the silica particle.

6. The oral care composition of claim 3, wherein the vitamin B1 molecule is chemically reacted with the surface of the silica particle.

7. The oral care composition of claim 1, wherein the composition comprises a dentifrice, a chewing gum, a mouthwash, or a mixture thereof.

8. The oral care composition of claim 7, wherein the composition is a dentifrice selected from the group consisting of toothpastes, tooth powders, denture creams and mixtures thereof.

9. The oral care composition of claim 1, further comprising at least one material selected from the group consisting of thickening agents, whiteners, abrasive agents, flavorants, humectants, detergents, surfactants, fluoride supplying compounds, desensitizing agents and mixtures thereof.

10. The oral care composition of claim 1, further comprising at least one additional cationic antibacterial agent.

11. The oral care composition of claim 1, wherein the cationic compatible metal oxide comprises silica particles with the vitamin B1 molecule immobilized on the surface of the silica particles so as to form vitamin B1 treated silica particles, said vitamin B1 treated silica particles having a % cetyl pyridinium chloride (CPC) compatibility of at least 10%, wherein % CPC compatibility indicates a molar percentage of CPC in a test solution resulting from (i) contacting 3 grams of the vitamin B1 treated silica particles with 27 grams of a 0.3 wt % CPC solution for 7 days at 140° F. to form a heated solution, (ii) cooling the heated solution to form a cooled solution, (iii) centrifuging the cooled solution at 10,000 rpm for 10 minutes to form two phases comprising the vitamin B1 treated silica particles and a separated solution, (iv) extracting a 1.0 gram sample of fluid from the separated solution, and diluting the 1.0 gram sample of fluid with deionized water at a ratio of 20 parts deionized water to 1 part sample of fluid.

12. The oral care composition of claim 1, wherein the amount of vitamin B1 molecule immobilized on the surface of the silica particle ranges from about 0.5 to about 1.0 wt % of the silica particle.

13. An oral care composition comprising: (1) an antibacterial effective amount of at least one cationic antibacterial agent, wherein the cationic antibacterial agent is cetyl pyridinium chloride (CPC); and (2) a cationic compatible metal oxide comprising (i) a silica particle and (ii) a vitamin B1 molecule immobilized on a surface of the silica particle so as to form a vitamin B1 treated silica particle, the vitamin B1 molecule (a) comprising (i) a vitamin B1 or (ii) a salt of a vitamin B1, and (b) being present in an amount sufficient to repel or minimize any reaction of the silica particle with said cetyl pyridinium chloride (CPC).

14. An oral care composition comprising (i) a dentifrice selected from the group consisting of toothpastes, tooth powders, denture creams, and mixtures thereof, (ii) a chewing gum, (iii) a mouthwash, or (iv) a mixture of any of (i), (ii) and (iii), said dentifrice, chewing gum, or mouthwash comprising a combination of: (1) an antibacterial effective amount of cetyl pyridinium chloride (CPC); and (2) a cationic compatible metal oxide comprising (i) a silica particle and (ii) a vitamin B1 molecule immobilized on a surface of the silica particle so as to form a vitamin B1 treated silica particle, the vitamin B1 molecule (a) comprising (i) a vitamin B1 or (ii) a salt of a vitamin B1, and (b) being present in an amount sufficient to repel or minimize any reaction of the silica particle with said cetyl pyridinium chloride (CPC).

* * * * *